United States Patent
Dottery et al.

(10) Patent No.: US 9,157,801 B2
(45) Date of Patent: Oct. 13, 2015

(54) LASER DETECTION SYSTEM HAVING AN OUTPUT BEAM DIRECTED THROUGH A TELESCOPE

(75) Inventors: Ed Dottery, Palm Harbor, FL (US); Kenneth Pohl, Clearwater, FL (US); Darius Vunck, Clearwater, FL (US); Robert Waterbury, Palm Harbor, FL (US); Frank Vilardi, Largo, FL (US)

(73) Assignee: Alakai Defense Systems, Inc., Largo, FL (US)

( * ) Notice: Subject to any disclaimer, the term of this patent is extended or adjusted under 35 U.S.C. 154(b) by 70 days.

(21) Appl. No.: 13/529,722

(22) Filed: Jun. 21, 2012

(65) Prior Publication Data
US 2013/0293882 A1    Nov. 7, 2013

Related U.S. Application Data

(60) Provisional application No. 61/499,447, filed on Jun. 21, 2011.

(51) Int. Cl.
| | |
|---|---|
| G01J 3/44 | (2006.01) |
| G01J 3/02 | (2006.01) |
| G01N 21/65 | (2006.01) |
| G01N 21/17 | (2006.01) |

(52) U.S. Cl.
CPC ............... *G01J 3/44* (2013.01); *G01J 3/0235* (2013.01); *G01J 3/0289* (2013.01); *G01N 21/65* (2013.01); *G01N 2021/1793* (2013.01)

(58) Field of Classification Search
CPC ............... G01J 3/0218; G01J 3/4406–3/4412; G01J 3/44; G01J 3/0289; G01J 2003/44–2003/4424; G01N 21/65; G01N 2021/65–2021/655; G01N 2021/1793–2021/1797
USPC ............ 356/300–334; 250/339.07; 359/379, 359/380, 432
See application file for complete search history.

(56) References Cited

U.S. PATENT DOCUMENTS

| | | | | |
|---|---|---|---|---|
| 3,779,492 | A | * | 12/1973 | Grumet ........................ 244/3.17 |
| 4,680,745 | A | | 7/1987 | Ota et al. |
| 4,870,275 | A | | 9/1989 | Ozdemir |
| 5,524,845 | A | * | 6/1996 | Sims et al. .................. 244/3.17 |
| 6,996,135 | B2 | | 2/2006 | Martinelli et al. |

(Continued)

OTHER PUBLICATIONS

Five-wavelength LiDAR, Centre for Atmospheric Science—The University of Manchester, 3 pages.

*Primary Examiner* — Michael A Lyons
*Assistant Examiner* — Violeta A Prieto
(74) *Attorney, Agent, or Firm* — Christopher Paradies; Paradies Law P.A.

(57) ABSTRACT

A system comprises a processing system, a laser system, a telescope system, a detector system and optical systems operatively arranged such that the laser system may be capable of outputting multiple wavelengths to a common telescope system, and the detector system is capable of receiving signatures from the same telescope system, under the control of a control system. The processor system processes signals received from the detector system to determine substances identified by known signatures. For example, a plurality of detectors in the detector system each receive a range of wavelengths of the signatures received by the telescope system. For example, a variable beam diverger and variable beam expander operatively control expansion and divergence of the output the laser system. For example, a beam reducer and lenslet array may operatively transmit signatures via optical fiber bundle to one or more of the detectors.

20 Claims, 19 Drawing Sheets

(56) References Cited

U.S. PATENT DOCUMENTS

| | | |
|---|---|---|
| 7,064,887 B2 | 6/2006 | Mongardien et al. |
| 7,274,801 B2 * | 9/2007 | Lee .................. 382/103 |
| 7,583,364 B1 | 9/2009 | Mayor et al. |
| 7,869,469 B1 | 1/2011 | Spuler |
| 8,009,288 B2 | 8/2011 | Berlin et al. |
| 8,072,595 B1 * | 12/2011 | Bastiaans et al. ............ 356/301 |
| 8,169,717 B2 * | 5/2012 | Caldwell .................. 359/749 |
| 8,254,023 B2 * | 8/2012 | Watson et al. ............... 359/432 |
| 2002/0034000 A1 * | 3/2002 | Hoult et al. ................. 359/350 |
| 2002/0063113 A1 * | 5/2002 | Wiggermann et al. ..... 219/121.7 |
| 2004/0130896 A1 * | 7/2004 | Brown et al. ................ 362/259 |
| 2004/0257563 A1 * | 12/2004 | Miller et al. ................ 356/328 |
| 2006/0092995 A1 | 5/2006 | Frankel et al. |
| 2006/0227415 A1 * | 10/2006 | Caldwell et al. ............ 359/432 |
| 2007/0076200 A1 * | 4/2007 | Martin et al. ................ 356/318 |
| 2007/0146506 A1 | 6/2007 | Lin et al. |
| 2008/0033275 A1 | 2/2008 | Blank et al. |
| 2008/0198365 A1 * | 8/2008 | Treado et al. .................. 356/73 |
| 2008/0198451 A1 * | 8/2008 | Gohman et al. ............. 359/432 |
| 2009/0137544 A1 | 5/2009 | Li |
| 2009/0161244 A1 * | 6/2009 | Hirose et al. ................... 360/31 |
| 2009/0237648 A1 | 9/2009 | Armstrong et al. |
| 2009/0237810 A1 * | 9/2009 | Frazier et al. ............... 359/744 |
| 2010/0085567 A1 * | 4/2010 | Dottery et al. .............. 356/301 |
| 2010/0171820 A1 * | 7/2010 | Hendriks et al. ............... 348/65 |
| 2010/0177929 A1 * | 7/2010 | Kurtz et al. ................. 382/103 |
| 2010/0316382 A1 | 12/2010 | Litvin |
| 2011/0013267 A1 | 1/2011 | Griseri et al. |
| 2011/0069380 A1 * | 3/2011 | Sprenger ..................... 359/375 |
| 2012/0099102 A1 | 4/2012 | Bello |
| 2013/0128261 A1 * | 5/2013 | Pohl et al. ..................... 356/51 |

* cited by examiner

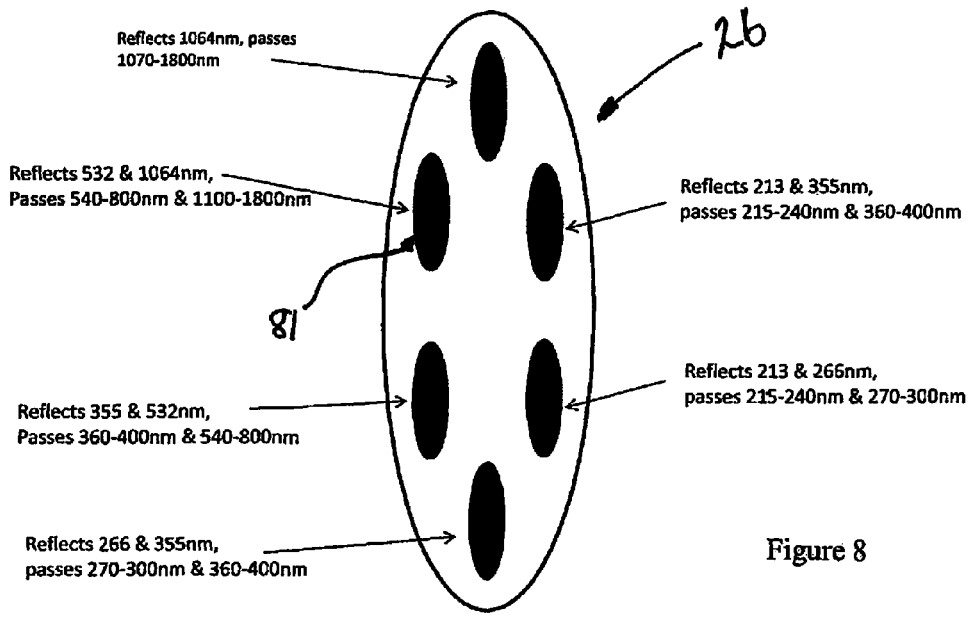
Figure 8
Figure 9
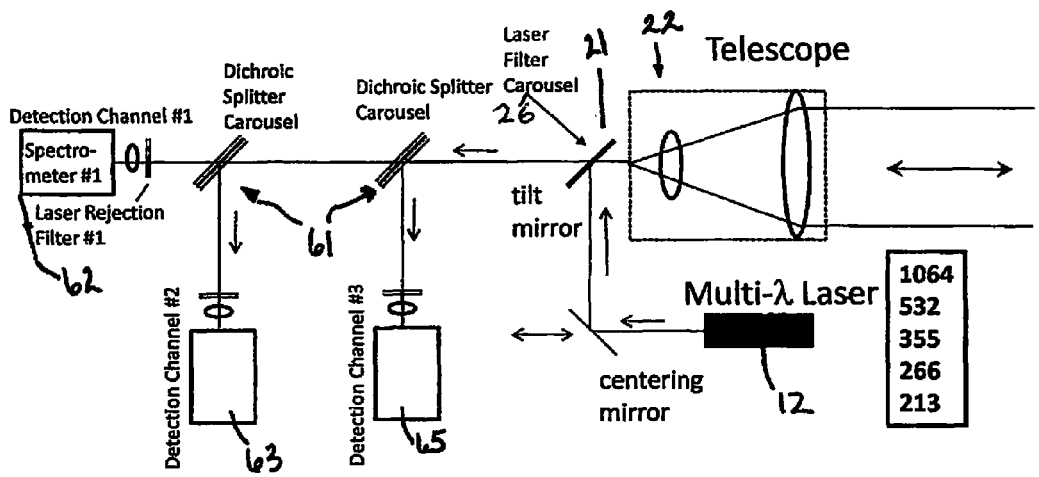

LASER DETECTION SYSTEM HAVING AN OUTPUT BEAM DIRECTED THROUGH A TELESCOPE

CROSS-RELATED APPLICATIONS

The application claims priority to the filing date of U.S. Provisional Appl. No. 61/499,447, which was filed Jun. 21, 2011, and U.S. Provisional Appl. No. 61/499,447 is hereby incorporated by reference herein in its entirety.

FIELD OF THE INVENTION

The field relates to laser spectroscopy.

BACKGROUND

The Applicant has already filed provisional application number 60/914,658 on Apr. 27, 2007 to a laser plasma spectroscopy system, which is now incorporated by reference in U.S. application Ser. No. 12/597,761. The examples disclosed in these applications stimulate plasma to enhance a detected signal at a stand-off distance from which chemicals at or near a surface may be sampled. The disclosures of these applications are hereby incorporated by reference in their entirety.

A key design parameter of a RAMAN spectroscope is the wavelength' of the laser, which is typically optimized for specific conditions and for a particular application. In U.S. Pat. Publ. No. 2011/0013267, published Jan. 20, 2011, and filed Jul. 17, 2009, a RAMAN pump light source is activated at a plurality of pump wavelengths and power levels such that only one pump wavelength is active at any given pump power level, achieving amplification gain in an optical fiber probe by backward propagation amplification. This technique is useful for configuring a RAMAN distributed amplifier for optical network equipment. However, RAMAN interaction may cause deleterious effects, including RAMAN scattering, crosstalk, non linear distortions, increased noise levels, distortion, unacceptable carrier to noise ratios and attenuation. See U.S. Pat. Publ. No. 2010/0316382, which published Dec. 16, 2010 and was filed Jul. 11, 2009, which discloses a method of back-pumped distributed RAMAN amplification using an unmodulated laser of an appropriate wavelength at the distal end of a fiber far from the opposite end where co-propagating signals are launched.

U.S. Pat. No. 6,996,135 discloses a cascaded RAMAN laser with wavelength selectors and an intercavity section that is made of a non-linear optical medium, resulting in multi-wave mixing amplification, transferring energy from radiation with shorter wavelengths to radiation with longer wavelengths more efficiently.

U.S. Publ. No. 2009/0137544, published May 28, 2009 and Dec. 10, 2007, claimed priority to several provisional applications and disclosed a multimodal multiplex multi-wavelength RAMAN spectroscopy system for high through-put fluorescence for detecting alcohol in tissue and cholesterol testing in Zebra fish embryos. The sensor included a combination of spatially coded detecting optics and spectrally coded excitation sources to get a RAMAN spectrum of alcohol in tissue, from 1600 to 1000 $cm^{-1}$.

U.S. Pat. No. 4,680,745 issued Jul. 14, 1987 and disclosed an optical system using variable beam expanders and other optical elements for recording pits and grooves on a surface of a recording medium. Light having different wavelengths for the pits and grooves was disclosed.

A five-wavelength LiDAR system was used by the Centre for Atmospheric Science at the University of Manchester, which was designed by Flight lasers of Germany using a Continuum PL8020 Nd:YAG laser in conjunction with a multiplexer to pump Raman shifting cells to produce wavelengths of 266, 289, 299, 316 or 315 nanometers. Wavelengths of 289, 299 and 316 nanometers are generated by stimulated Raman scattering in three respective Raman cells. The system uses the five wavelength beams to measure attenuation and to calculate the vertical distribution of ozone and aerosols in the atmosphere.

U.S. Pat. No. 4,870,275 issued Sep. 26, 1989 and disclosed remote detection of gases in the atmosphere using a Raman-shifted excimer/dye laser beam through a circulating-medium Raman-shifting cell, allowing an infinite number of different wavelengths of emitted radiation for measurement. Wavelengths are emitted in absorbed and non-absorbed ranges to calculate the presence and quantity of gases in the atmosphere. U.S. Pat. No. 7,583,264 issued Sep. 1, 2009 and disclosed an eye-safe atmospheric aerosol LIDAR using a stimulated Raman scattering gas cell and non-focused laser beam geometry. U.S. Pat. No. 7,869,469 issued Jan. 11, 2011 and discloses a Raman shifter with improved optical efficiency and robustness including a source system having a source pump laser and a seed laser, which are combined for transmission into a Raman cell having a multi-pass pathway through the cell using a medium that is circulated in a direction transverse to the beam pathways. U.S. Pat. No. 8,009,288 issued Aug. 30, 2011 and disclosed a system containing a stimulated Raman or coherent anti-Stokes Raman spectroscopy system using a resonant cavity containing a sample of a nucleic acid derivative in solution for analysis and sequencing of the nucleic acid.

U.S. Publ. No. 2006/0092995 published May 4, 2006 and discloses a multi-wavelength, commonly mode-locked external cavity laser system. A wavelength-selective device controllably transmits or reflects diffracted optical beams depending on the wavelength. U.S. Publ. No. 2007/0146506 published on Jun. 28, 2007 and disclosed a system for determining the vignetting function of an image and using the function to correct for vignetting if present.

U.S. Publ. No. 2009/0237648 published Sep. 24, 2009 and discloses a system for performing Raman spectrometry mounted on a vehicle using dual pulsed beams at a first wavelength and a second wavelength to identify a target by matching a Raman signature with a given collected Raman spectra. The system is used for detecting chemical or biological agents under a vehicle or at a short distance (e.g. up to 1.5 meters). According to the reference, 1.5 meters is considered a "standoff range." To be considered a "stand off distance" in this application, a system must be able to identify a target at a distance up to and including forty (40) meters. A system having a range for identifying a target less than 40 meters is not considered as operating at a stand off distance, notwithstanding the suggestion in U.S. Publ. No. 2009/0237648, which teaches that there is still a need for improvements in stand-off on-the-move detection systems. Applicant agrees that there is still a need for improvement but disagrees that a range up to 1.5 meters provides for stand off detection as that term is defined herein.

U.S. Publ. No. 2012/0099102 published Apr. 26, 2012 and discloses probes for focusing outputs from a plurality of light sources or lasers onto a sample and collecting backscattered radiation from the sample, separating Raman spectra from backscattered light and providing at least on output containing the Raman spectra. This publication teaches that fiber optic Raman probes offer favorable configurations, but teaches that there is a need for increased efficiency, accuracy and accessibility in Raman measurements, such as to avoid interference from luminescence or fluorescence bands, to provide spectra in regions where detectors having their maximum response and to provide probes that are compact or handheld. The disclosed device enables a Raman spectra of two or more excitation wavelengths to be obtained simultaneously. As an example, the publication discloses two excitation laser sources and one or more spectrographs receiving Raman signals via one or more fiber optic channels.

None of the sensors, amplifiers or detectors of the known references disclose, teach or suggest a multi-wavelength laser capable of use in RAMAN spectroscopy suitable for use at stand off distances and/or using a laser capable for use as a component of a system capable of being used for neutralization of a threat.

SUMMARY

A multi-wavelength laser provides output laser wavelengths ranging from the deep UV to near IR, providing a very flexible RAMAN system, which can collect RAMAN spectra, at multiple laser wavelengths, for example. In one example, a system utilizes a high power Nd:YAG fiber laser such as a laser neutralization source (e.g. Thor or Zeus Nd:YAG lasers) capable of being used to neutralize a threat. A multi-wavelength head may be coupled to a high power laser system. The multi-wavelength head, high power laser system and sensors may be combined with telescopic optics to provide a laser detection system capable of detecting trace elements indicating the presence of explosives at stand-off distance, such as up to or greater than forty (4) meters, more preferably at least 50 meters, and even more preferably at least 100 meters, for example.

In one example, such a system is integrated with a high power neutralization laser system, which may be mounted on a vehicle, for example. An optical layout for a multi-wavelength RAMAN laser system may be integrated with high power neutralization laser systems without adding significant weight or bulk to the system, allowing the same mounting apparatus to be used without modification, for example.

In yet another example, the detector system may incorporate optical elements to redirect radiation emitted or scattered from a target surface toward one or more detectors integrated into a multi-wavelength detection system. For example, a multi-wavelength Raman laser detection system may comprise two, three or more than three detectors using one or more dichroic splitter carousels. Each dichroic splitter carousel may incorporate a plurality of optical elements for redirecting by reflection one or more ranges of wavelengths and transmitting one or more ranges of wavelengths.

In one example, a variable focal distance system is incorporated into a stand-off detection system, such as a Raman detector. The system directs an excitation beam through variable beam expander/variable beam diverger optics to a target using a telescopic optical system for both the outgoing excitation beam and the receiving path for collection of the signature from the target. The system is capable of capturing molecular signature radiation, using the same telescopic optical system and using a separate beam reducer and lenslet array optical system for directing the received signal into an optical fiber bundle for delivery of the received signature to one or more sensors, such as a spectrometer or spectrometers, for analyzing a received radiation signature. The telescope optical system comprises reflective mirrors, and the excitation beam is focused at different distances using the variable beam expander/diverger without vignetting that could otherwise be introduced without use of the variable beam expander/diverger and receiver optics.

The features of the various examples may be combined, such as to provide a system capable of variable focal distance for a one or more lasers, a multi-wavelength laser and a plurality of detectors, with one or more detection paths comprising a beam reducer/lenslet array/fiber bundle in the signal receiving path.

BRIEF DESCRIPTION OF THE DRAWINGS

FIG. 8 illustrates a laser filter carousel.

FIG. 9 illustrates another example of a system for simultaneous detection of a plurality of wavelengths, using a single telescope.

DETAILED DESCRIPTION

Figure 1:
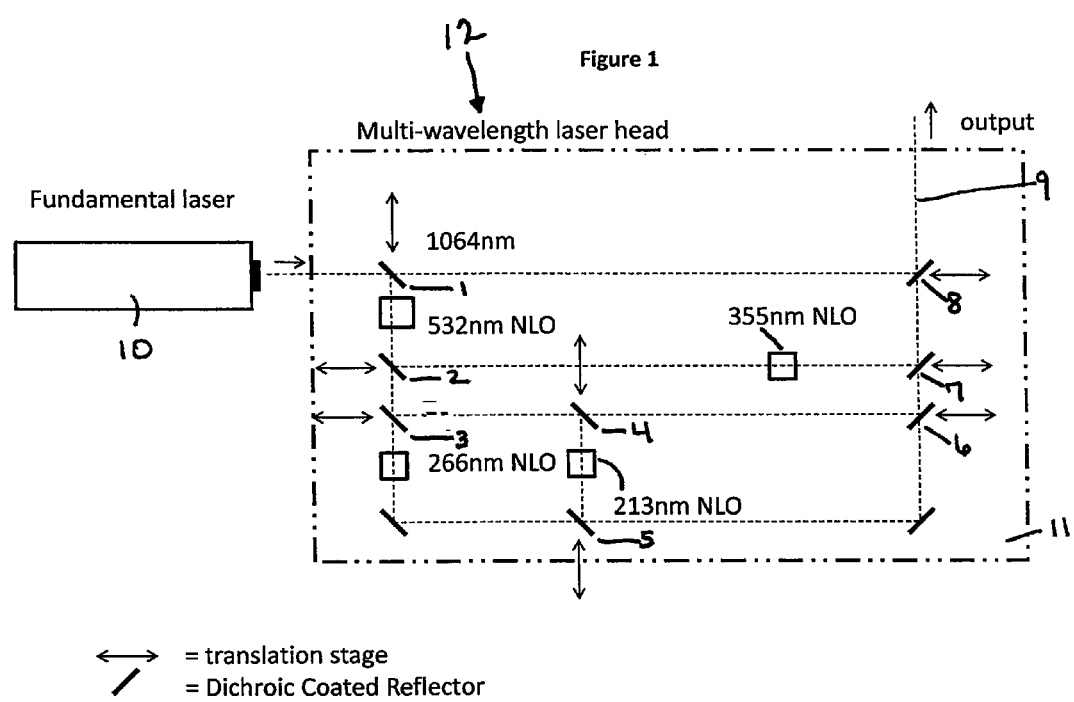
FIG. 1 illustrates a schematic representation of one example of a multi-wavelength RAMAN laser system.

An optical layout for a multi-wavelength RAMAN laser is illustrated in FIG. 1, using a Nd:YAG laser producing output radiation at 1064nm. This layout utilizes a plurality of Non-Linear Optical (NLO) elements for laser frequency conversion. These NLO's are arranged to generate a plurality of harmonics, such as up to 5 harmonics, individually or simultaneously, by introducing special dichroic coated mirrors or reflectors arranged to output one or more of the laser beams. The output wavelengths for this 1064 nanometer fundamental are 1064, 532, 355, 266 & 213 nanometers (nm), for example.

FIG. 1 shows a Nd:YAG laser as the fundamental laser with non-linear optical elements shifting wavelengths from the 1064 nm primary to 532 nm, 355 nm, 266 nm, and 213 nm, respectively. However, other laser technologies may be used, such as: Nd:YLF having output wavelength at 1047 nm with multiple outputs at 1047, 523, 349, 262 and 209 nm; Yb:YAG output wavelength at 1030 nm with multiple outputs at 1030, 515, 343, 257 and 206 nm, for example.

Figure 2:
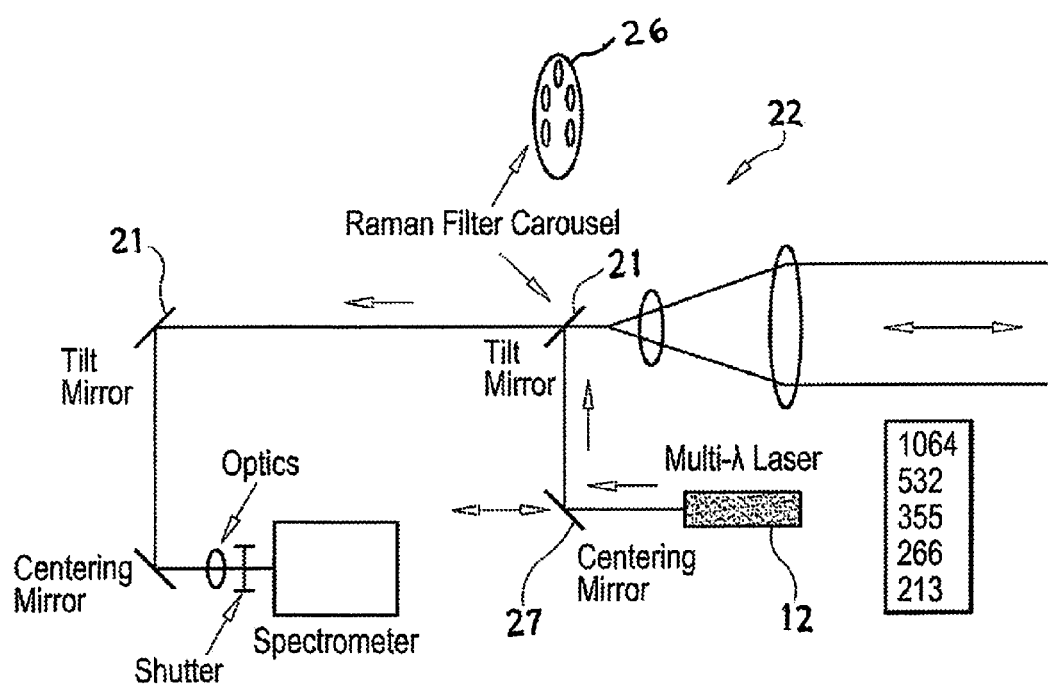
FIG. 2 illustrates a schematic of the RAMAN laser system incorporated in standoff RAMAN spectroscopy system utilizing a RAMAN filter carousel.
Figure 6:
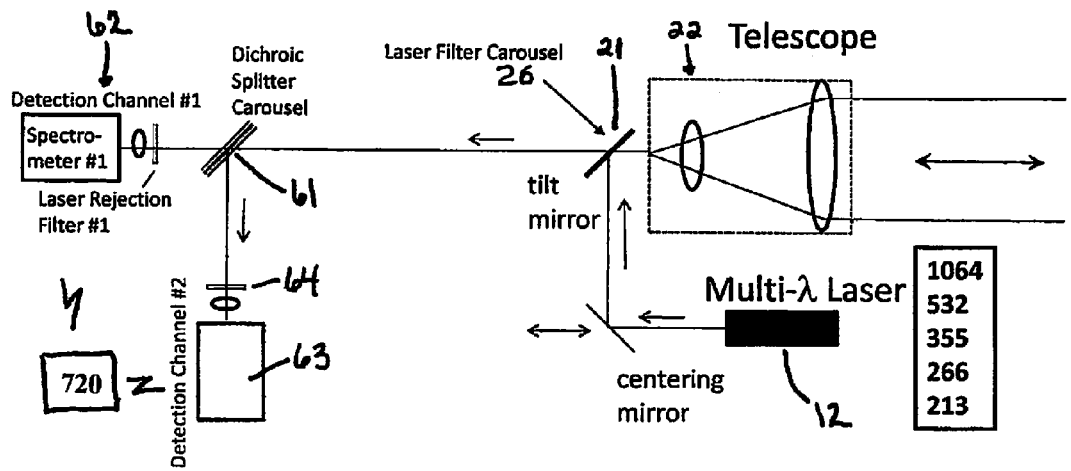
FIG. 6 illustrates an example of a system for simultaneous detection of 2 wavelengths using a single telescope.

For example, such a multi-wavelength RAMAN laser is mounted in a Standoff RAMAN Detection system, as illustrated in the example of FIG. 2. FIGS. 6 and 9 illustrate examples that utilize a single telescope and a plurality of detectors for detection of a plurality of wavelengths, simultaneously.

Figure 4:
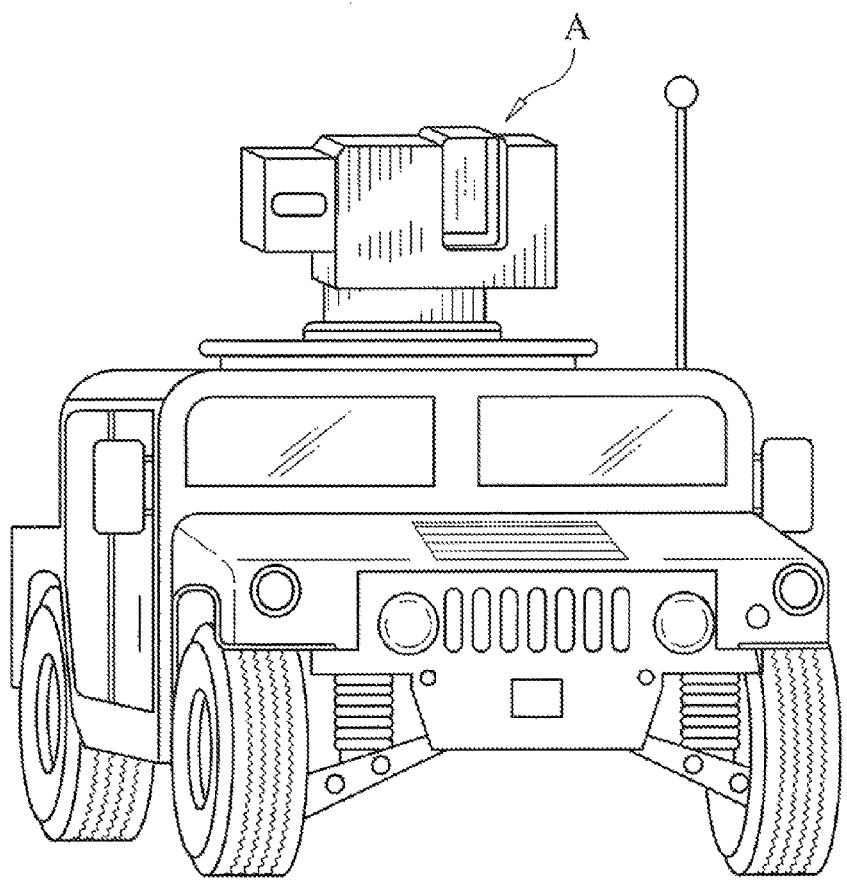
FIG. 4 is a photograph of a Zeus laser neutralization system.
Figure 5:
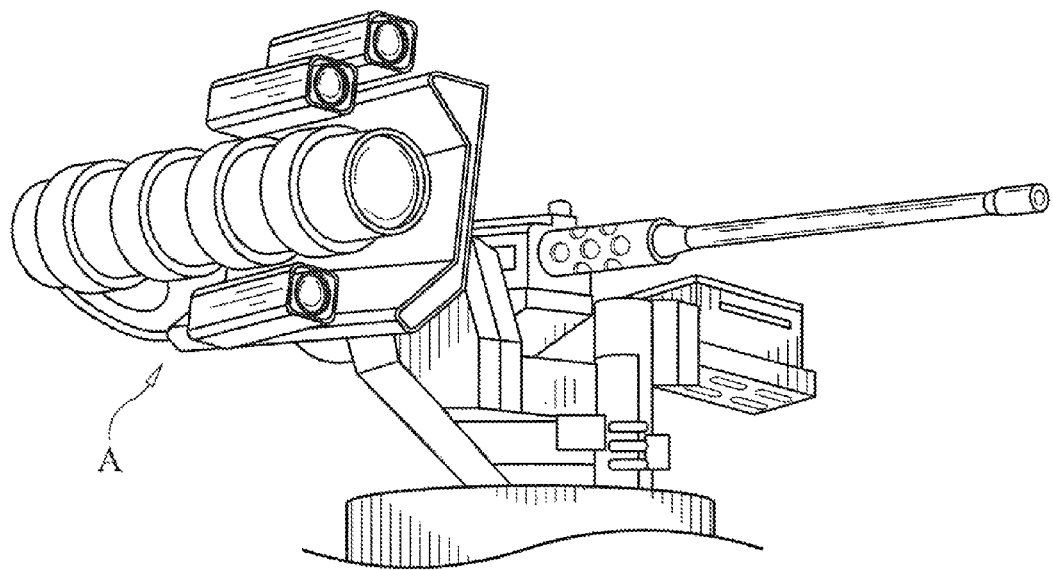
FIG. 5 is a photograph of a Thor laser neutralization system.

Non-Linear Optics may be used to produce the wavelength conversion. In alternative examples, RAMAN gas shifting cells or Optical Parametric Oscillators (OPO's) may be used to produce a plurality of wavelengths from a single wavelength laser. In one example, a high power neutralization laser A, A' such as shown in FIGS. 4 and 5 is used as the sole source for a multi-wavelength RAMAN laser head as illustrated in FIG. 1. A RAMAN detecting system as shown in FIG. 2 couples the single-wavelength laser of neutralization laser with an optical system that outputs a plurality of laser beams, each having a different wavelength for use in a standoff laser detecting system, using RAMAN spectroscopy. The laser 12 may be incorporated using a centering mirror 27, tilt mirror 21, and telescope optics 22, with a laser filter carousel 26 combined with the tilt mirror 21. The example is packaged into a system, A, A' just slightly larger than the systems A, A' shown in FIGS. 4 and 5, which incorporate the optics of FIGS. 1-3.

The system packaged together continues to operate as a neutralization system, while being operated as a standoff laser detecting system. The method is capable of switching from neutralization to detection by adjusting the optics in FIG. 1 to direct the laser beam 9 directly to the neutralization system, such as by displacing beam splitter 1, or example. Beam splitters 2, 3, 4, 5, 6, 7 and 8 may be capable of adjusting to direct the laser beam 9 through one or more of a plurality of non-linear optical instruments capable of providing a plurality of beams, each with a different wavelength for use in a RAMAN spectroscopic detector that utilizes the telescope of the laser neutralization system for standoff RAMAN spectroscopy. In one example, the integration of a detection system into a preexisting neutralization system may be accomplished without adding substantial bulk or weight, such that the mounting apparatus of the preexisting neutralization system may be used without modification. This may be accomplished by sharing the same high power laser, telescope optics and mounting apparatus as the preexisting neutralization system, which are the heaviest and bulkiest components of the system.

Figure 7:
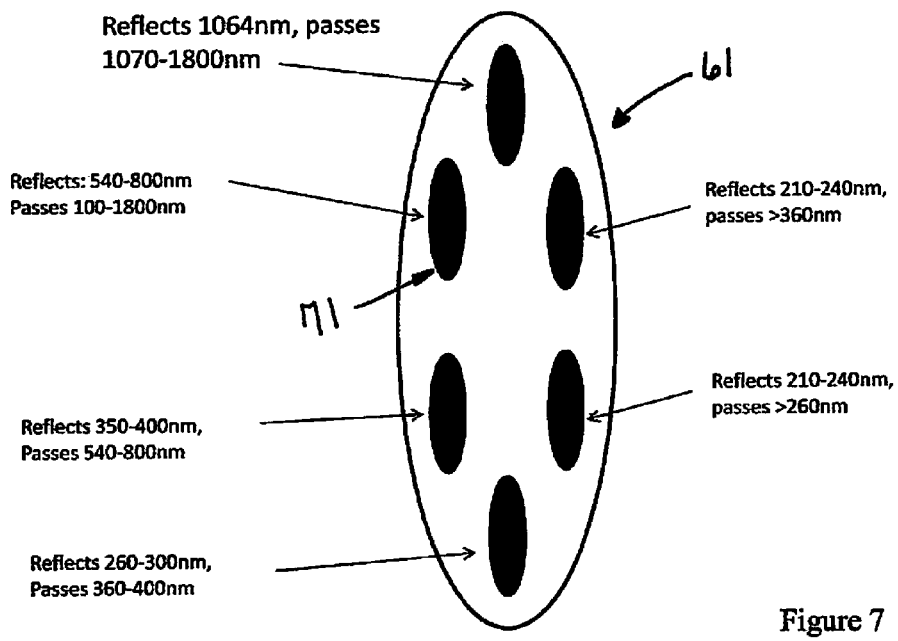
FIG. 7 illustrates a dichroic filter carousel.

FIG. 6 illustrates an example of a dichroic splitter carousel 61 arranged to direct wavelengths of scattered radiation toward one of two detectors 62, 63 designed for detecting an electromagnetic signature from a substance on a target surface. A filter 64 may be disposed between the detectors 62, 63 and the telescope 22 in order to filter out the electromagnetic radiation of the beams used for stimulating an electromagnetic signature from a substance on a target surface. For example, a multi-wavelength laser 12 may be incorporated into a system incorporating telescopic optics 22. FIG. 7 illustrates a detailed view of a dichroic splitter carousel 61.

Figure 3:
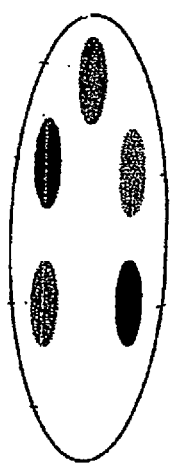
FIG. 3 illustrates a detail of a schematic view of a RAMAN filter carousel.

A plurality of dichroic filters 71 may be arranged on a rotatable carousel 61, as illustrated in the detail view of FIG. 3 and FIG. 7, for example. Each optical element of a plurality of optical elements may reflect one range of wavelengths while passing a second range of wavelengths. For example, a "reflect:pass" characterization for one of the dichroic optical elements includes an example of about 1064:1070-1800, which represents a reflection of a substantial portion of wavelengths of about 1064 nanometers, "about" meaning + or -3 nanometers and a "substantial" portion means a portion sufficient to operationally redirect a beam of a laser of that wavelength, for example, and a pass through filter for passing substantial electromagnetic radiation at wavelengths from 1070-1080 nanometers, "substantial" meaning an operatively effective percentage of such radiation for detecting the radiation at a spectrometer of the system. A person having ordinary skill in the art will understand that dichroic splitter optical elements are never perfectly reflective or perfectly transmissive (i.e. pass through). Instead, such optical elements are selected from those optical elements then existing or created to operatively reflect or transmit radiation of the particular range of wavelengths. Additional examples for optical element reflect:pass ranges (in nanometers) may include (i) 540-800:900-1800; (ii) 350-400:540-800; (iii) 260-300:360-400; (iv) 210-240:>260 (i.e. transmission of wavelengths greater than 260 nanometers); (v) 210-240:>360, for example.

Likewise, a polychroic filter carousel 26 may be arranged to reflect one or more wavelengths of radiation emitted by a multi-wavelength laser 12, for example, as illustrated in the detail example of FIG. 8. For example, a plurality of polychroic optical elements 81 having reflect/reflect : pass/pass may be arranged on a rotatable carousel including (in nanometers) (i) about 1064:1070-1800; (ii) about 532/about 1064: 540-800/1100-1800; (iii) about 355/about 532: 360-400/540-800; (iv) about 266/about 355: 270-300/360-400; (v) about 213/about 266: 215-240/270-300; (vi) about 213/about 355: 215-240/360-400.

In the example of FIG. 9, a filter carousel 26 is disposed operatively to redirect a laser beam or beams through telescopic optics 22 toward a target surface, such as the filter carousel example in FIG. 8. Radiation from the target radiation may be scattered, and a portion of the radiation from the target surface may be directed back through the telescopic optics. The filter carousel 12 optics may be selected to transmit (i.e. pass through) the laser filter carousel 26. A first splitter carousel 61 may be disposed operatively to redirect a portion of the transmitted radiation toward a first detector 65. A second splitter carousel 61 may be disposed to operatively redirect a portion of the radiation transmitted through the first splitter carousel 61 toward a second detector 63 and transmitting radiation to a third detector 62. By combining a plurality of splitter carousels and a plurality of detectors, any number of detectors may be integrated into a single detection system, such as a multiplex Raman detection system.

In yet another example, a system comprises at least one variable beam expander/variable beam diverger for preparing an output laser beam for excitation of targets, such as target surfaces, disposed at various distances from a telescope. For example, the beam of a laser is operatively transmitted through a variable beam expander 101 and a variable beam diverger 102 prior to being redirected by a tilt mirror 21 toward the telescope 22. The telescope 22 in this example comprises optical reflectors that focus the laser beam at a distance depending on the variable beam expander/variable beam diverger optical elements 101, 102, such as from 25 meters to 300 meters, for example, as illustrated in FIGS. 11A-D. A fixed input from a laser enters the variable beam expander 101 that is adjusted depending on the target range and enters a variable beam diverger 102. The beam exiting the variable beam diverger 102 exits with a divergence angle and enters the telescope 22 and is incident at the telescope secondary, in order to provide a collimated laser output from the telescope 22 upon reflecting off the primary mirror of the telescope, for example.

Figure 10:
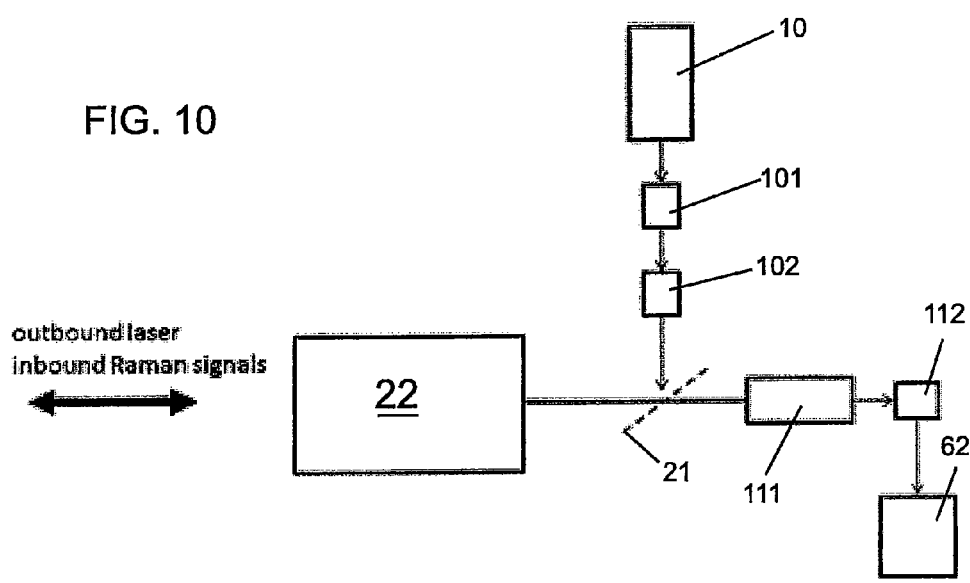
FIG. 10 illustrates another example of a system using a multi-mode reflective mirror telescope.
Figure 11:
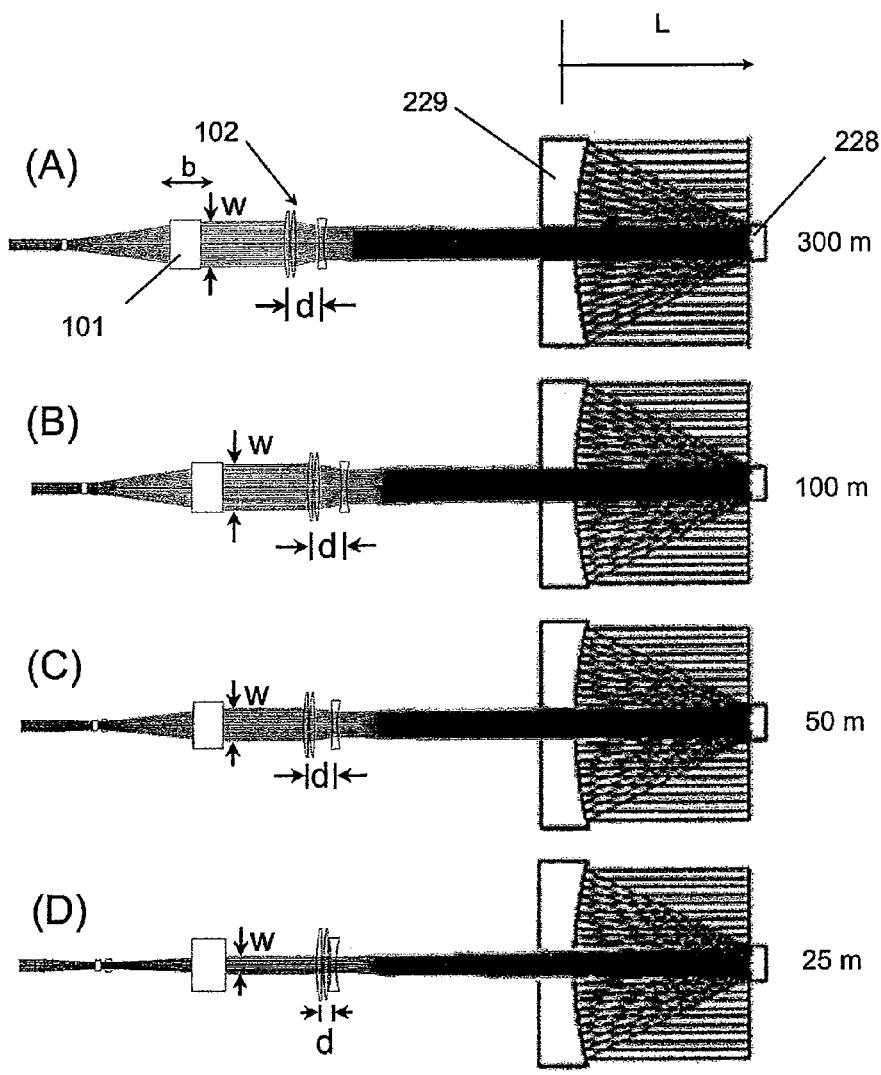
FIGS. 11A-D compare examples of a variable beam expander/variable beam diverger of the output excitation beam for focal lengths of from (A) 25 meters; (B) 50 meters; (C) 100 meters; and (D) 300 meters.
Figure 12:
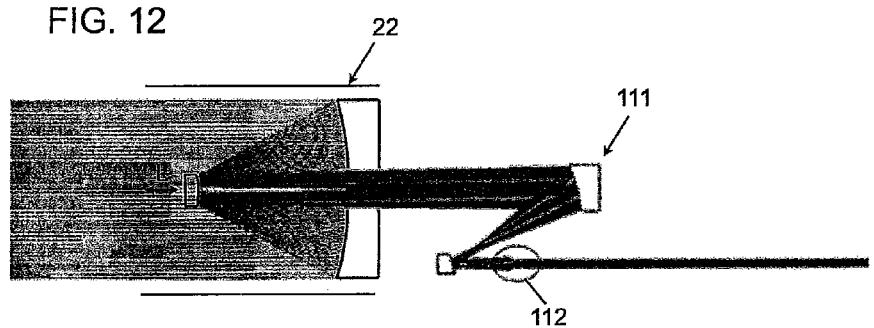
FIGS. 12 and 13 illustrate an example of the receipt of a signal and direction of the signal on the receiving side to a beam reducer and a detail view of a portion of FIG. 12 showing a lenslet array coupled to an optical fiber bundle.
Figure 13:
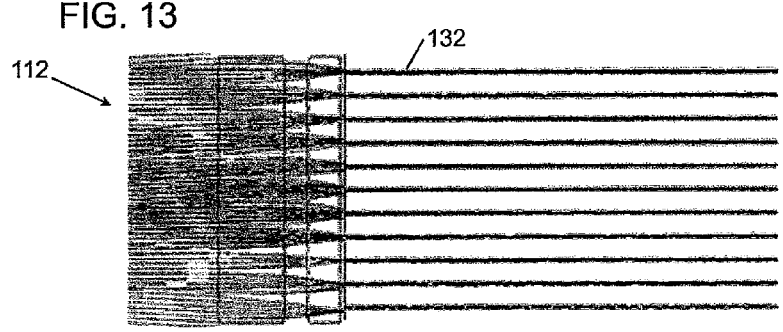

Alternatively, the beam divergence may be set such that the beam focuses at a selected target distance. In this example, as the target range changes, the telescope focus may be matched by adjusting operatively the variable beam expander and variable beam diverger, preventing vignetting. As illustrated in FIG. 12 and confirmed in FIGS. 14A-B, the path of the receiver remains collimated as it enters and exits the telescope 22 and is directed to a beam reducer 111, which may be a fixed beam reducer. The beam reducer 111 directs the beam exiting the telescope, after being transmitted through the tilt mirror 21 of FIG. 10, for example. The reduced beam is incident on a lenslet array 112 and onto a fiber bundle 132, as illustrated in the detail of FIG. 13, for delivery of the signal to a sensor or sensors, such as the Raman spectrometer 62 of FIG. 10, for example.

Figure 14A:
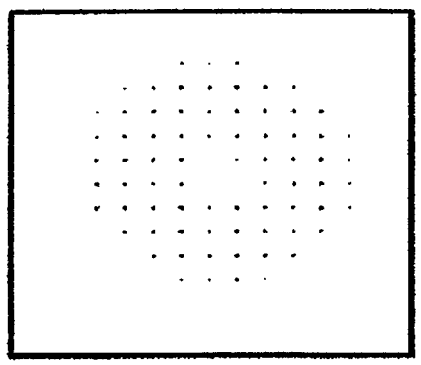
FIGS. 14A and 14B illustrate examples of collection percent efficiency, calculated as the percentage of energy from a fiber bundle into a detector compared to the energy incident at the telescope primary, showing a high collection percent efficiency of (A) 92% from a fiber bundle into a detector for a 150 millimeter target at 100 meters and (B) 94% from fiber bundle into a detector for a 12 millimeter target at 100 meters.
Figure 14B:
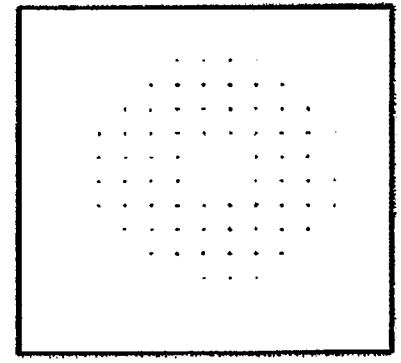
Figure 15:
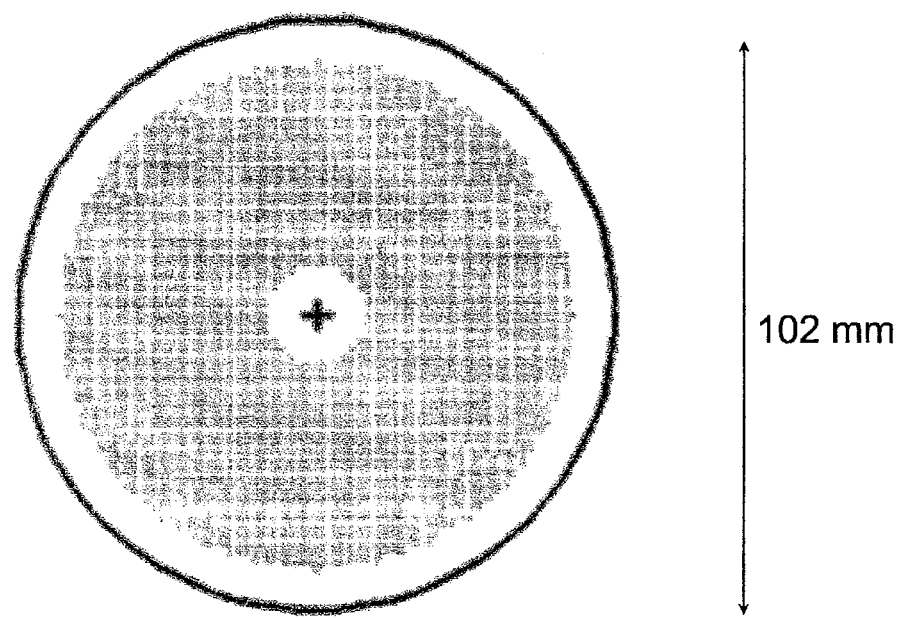
FIGS. 15A-D illustrate an example comparison of beam footprint plots of output of an excitation laser at various ranges showing calculated throughputs as percentage of rays at (A) 25 meters; (B) 50 meters; (C) 100 meters; and (D) 300 meters.
Figure 15:
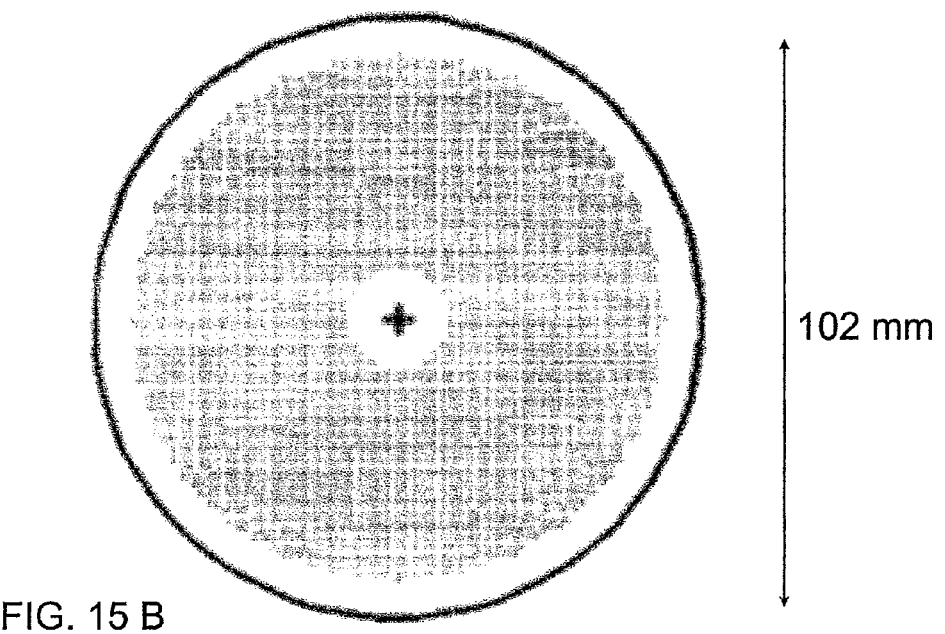
Figure 15C:
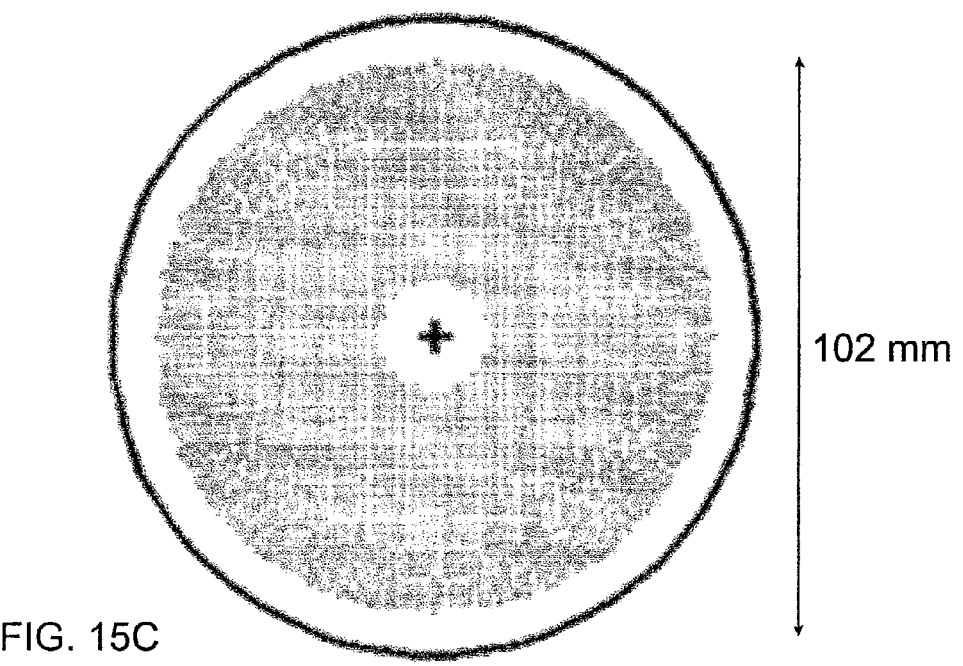
Figure 15:
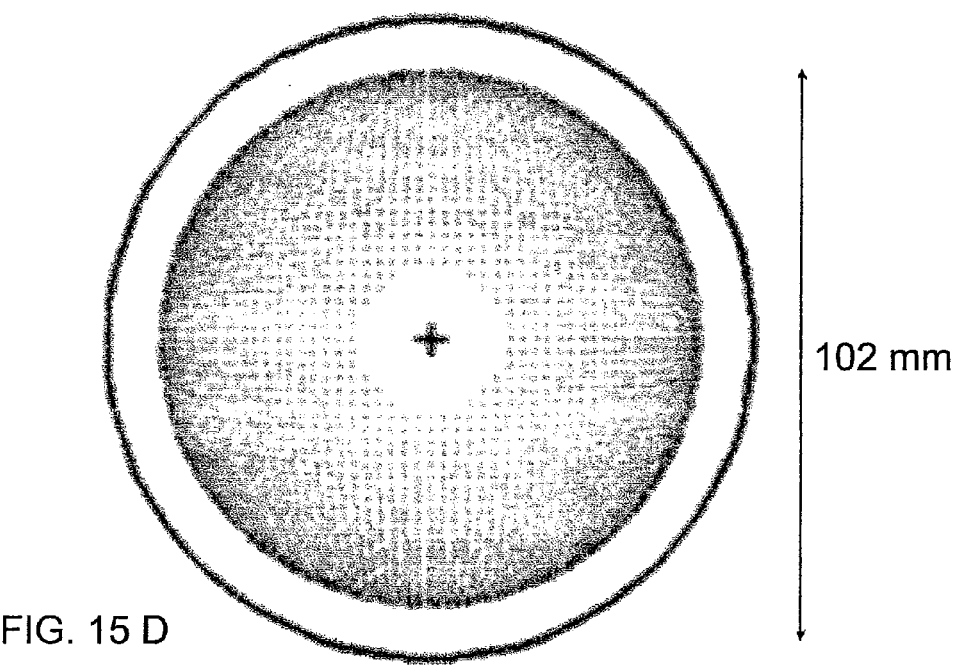

For example, the lenslet array may be a 10×10 square lenslet array supplying a fiber bundle of 81 fibers, discarding the corner areas of the square array to provide a circular array of optical fibers, as shown in the example of FIGS. 14A and 14B. The bundle of fibers may be rearranged as a linear column of 81 fibers (i.e. a 1×81 array) for input into a spectrometer linear aperture slit, for example. The collimated receive path results in a coupling efficiency that is insensitive to target size, for example, as illustrated in the comparison of FIGS. 14A-B, which shows comparable efficiency at 100 meters for both (A) a 150 millimeter diameter target and (B) a 12 millimeter diameter target.

FIGS. 15A-D illustrate results showing beam footprints at ranges of (A) 25 meters; (B) 50 meters; (C) 100 meters; and (D) 300 meters and calculated throughputs as a percentage of rays transmitted to a target as a output by the source, as calculated using computer aided design of optical modeling programs, such as Zemax, of (A) 96.25%; (B) 96.25%; (C) 96.53%; and (D) 92.30%, without consideration of attenuation of the beam by the environment through which the beam passes (i.e. the atmosphere). These figures and calculations shows that the collimated beam in this example substantially retains its intensity from emission for targets located at up to 300 meters, when collimated by setting the appropriate variable beam expansion and divergence, for example.

Figure 16:
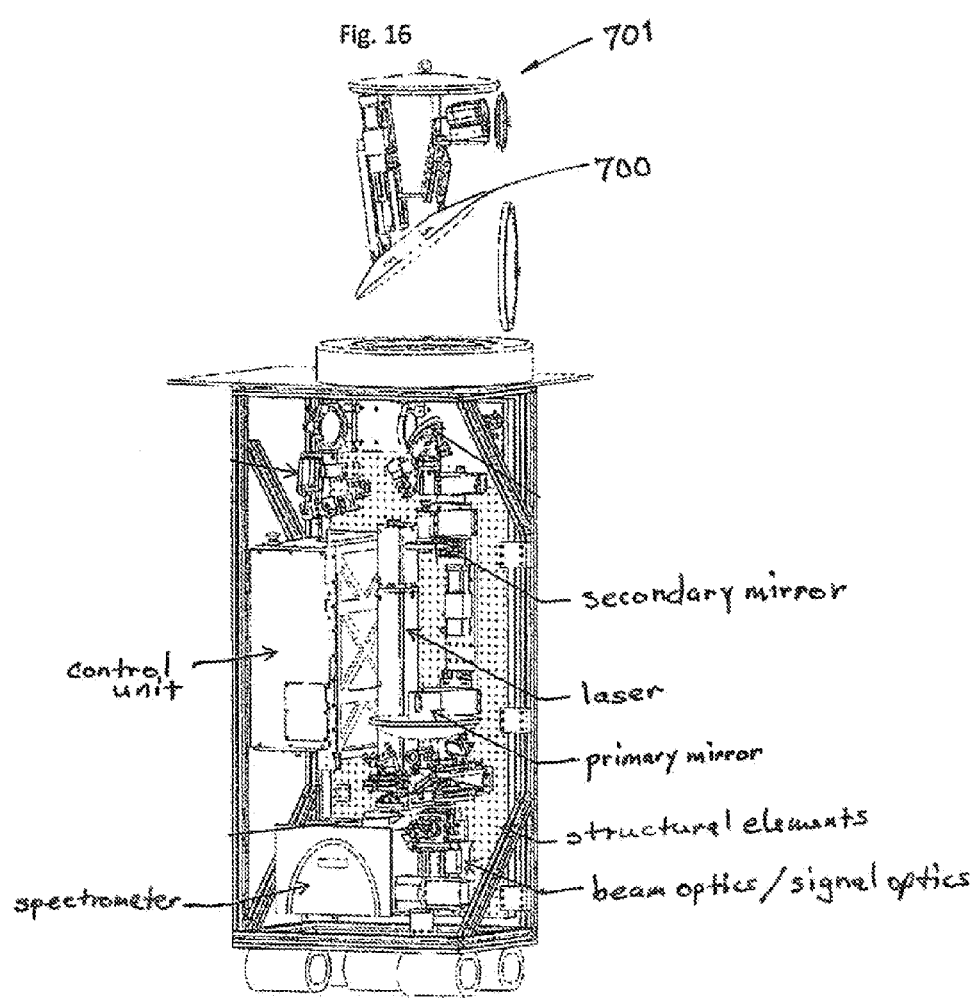
FIG. 16 illustrates an example of a laser detection system integrating two different lasers within a single laser detection system, wherein the two lasers synergistically enhance the sensitivity and range of the laser detection system in a field environment.
Figure 17:
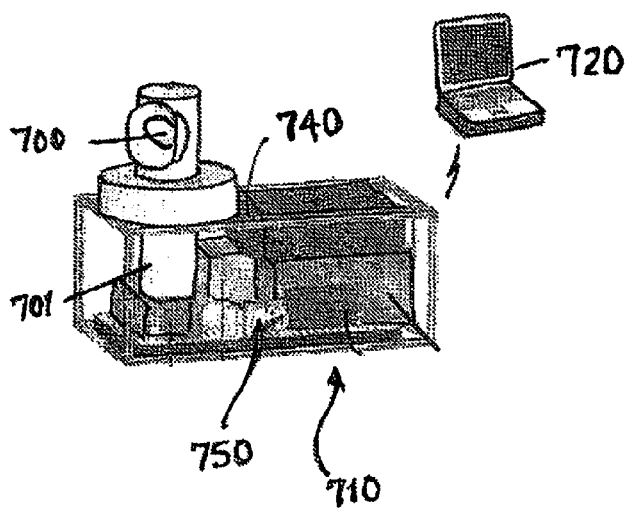
FIG. 17 illustrates another example of a laser detection system, schematically showing a compact configuration with targeting head optics including a rotatable and tiltable mirror for directing the output beam azimuth and elevation without moving anything except the targeting head optics.
Figure 18:
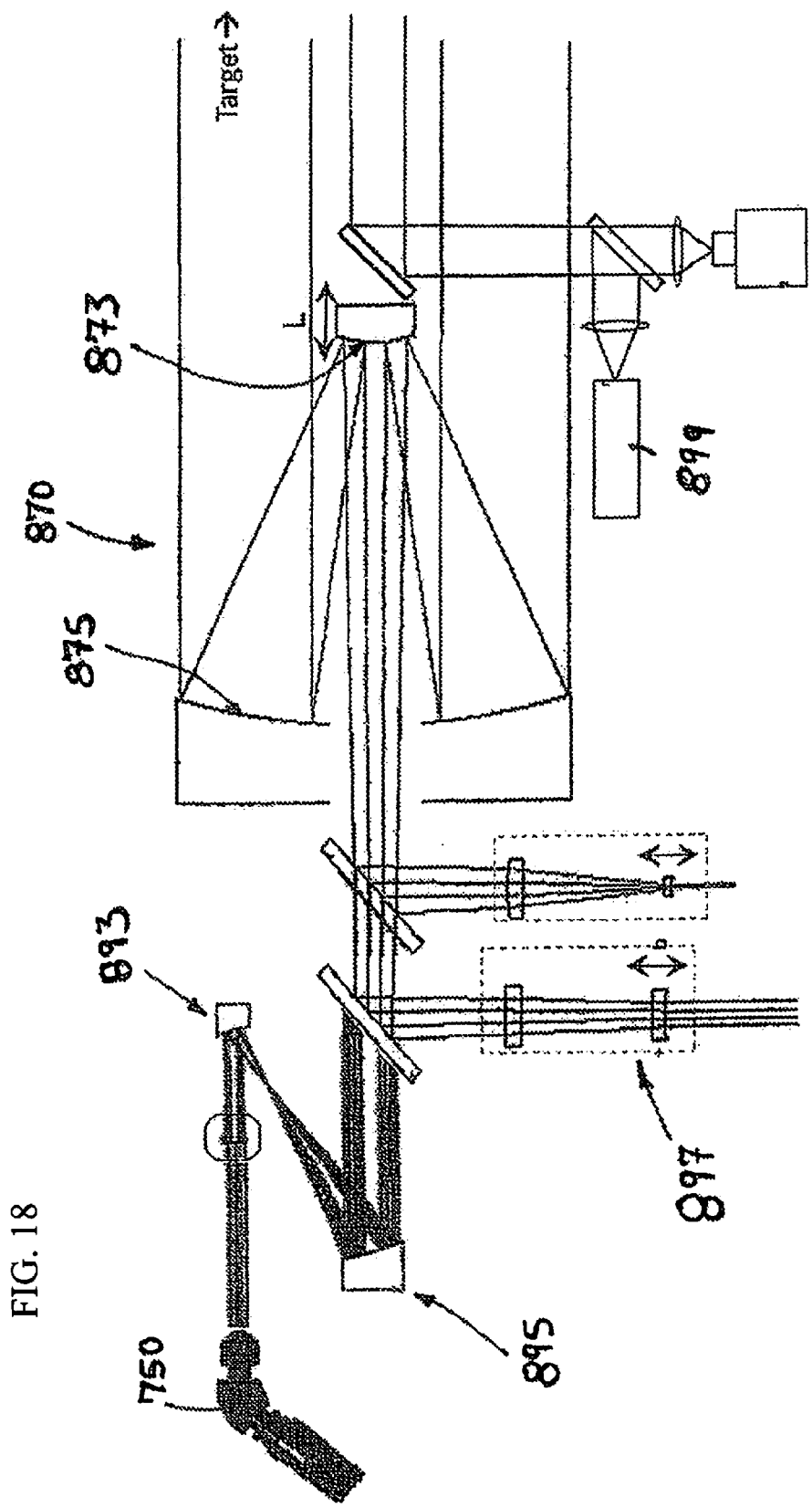
FIG. 18 illustrates yet another example of a laser detection system utilizing a Dall-Kirkham telescope with a six inch mirror arranged with a targeting optics head and a gaze aversion beam at a different wavelength than the output beam of the laser detection system such that the combined output beam and gaze aversion beam are eye safe, when the output beam of the laser detection system would otherwise not be eye safe.

Even though the field angles increase with decreasing range to a target, the receive path of the incoming signature is collimated. The lenslet focusing elements efficiently collect and couple the signal from the receive path to the optical fiber bundle, which is capable of maximizing fill factor and arranging an extremely short final focus into the optical fiber bundle array and minimizing any "lever arm" effect due to field angle, as illustrated in the comparison illustrated in FIGS. 14A and 14B, for example. FIG. 16 illustrates an example of a laser detection system integrating a rotatable and tiltable targeting mirror 700 into a targeting head package. FIG. 17 illustrates another example of a laser detection system 710, schematically showing a compact configuration with targeting head optics 701 including a rotatable and tiltable mirror 700 for directing the output beam azimuth and elevation, using control unit 720 operably coupled (wirelessly) to bus 740, without moving anything except the targeting head optics 701. FIG. 18 illustrates yet another example of a laser detection system utilizing a Dall-Kirkham telescope 870 with a six inch mirror 875 (primary) and a movably secondary mirror 873, arranged with a targeting optics head 701 and a gaze aversion system 899 having a gaze aversion beam at a different wavelength than the output beam of the laser system such that the combined output beam and gaze aversion beam are eye safe, when the output beam of the laser system would otherwise not be eye safe. Also, FIG. 18 illustrates spectrometer optics 750, 893,895 and output beam diverger/expander optics 897, which are adjustable relative to one another (arrows b).

Figure 19:
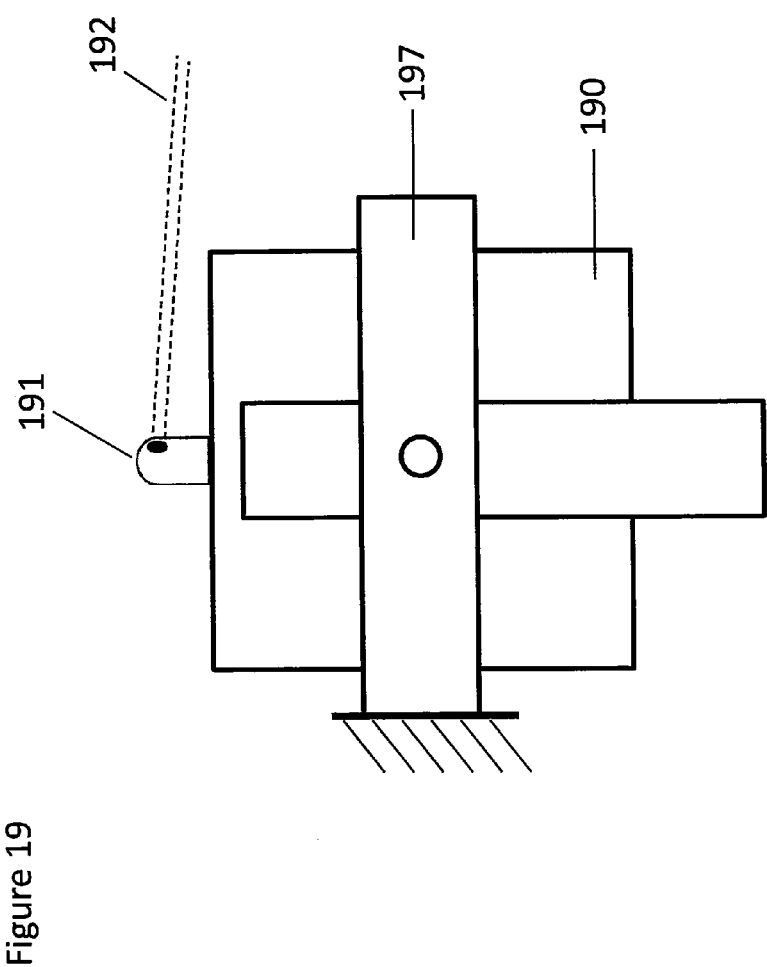
FIG. 19 illustrates yet another example.

FIG. 19 illustrates an example of an isolation system capable of isolating, to some degree, the laser detection system 190 from a surface represented by the diagonal lines, which may be a mounting surface in a vehicle, for example. The isolation system 197 may have a plurality of rotational axis, may include gyroscopic isolation and may include materials for reducing the transmission of vibrations to the laser detection system 190. Preferably, a laser targeting head 191 is capable of directing azimuth and elevation of an output beam 192 within useful limits compared to isolation system 197 without requiring any movement of other components of the laser detection system, such as the laser system, the telescope system, the detection system and the like. In one example, the targeting head 191 is electronically coupled with a targeting system, which may be connected by wire, fiber optics or wirelessly, such that the targeting system provides for manual or automatic target selection for the laser detection system. A manual target system may use a joystick or other user interface to select a target for the targeting system. An automated target selection system may adopt one or more of the known strategies for automatically selecting targets, such as random selection or computer-controlled selection based on identified threats. For example, U.S. Pat. No. 5,524,845, which issued Jun. 11, 1996; U.S. Pat. No. 7,274,801, which issued Sep. 25, 2007; and U.S. Pat. No. 3,779,492, which issued Dec. 18, 1973 disclose automated systems for target recognition and selection, and the disclosures and drawings for these references are hereby incorporated by reference in their entirety to illustrate state of the art target recognition and selection systems that are known and may be incorporated with a targeting system to control automatic recognition and selection of targets for directing the laser targeting head 191. A rangefinder may be used to determine the distance to a surface of a target, which may be used by a control unit to control components, such as variable beam expanding and diverging optics of the laser system, the disposition of the secondary mirror of the telescope system. Also, the rangefinder may be integrated with control systems to aid other systems, such as the autofocus systems for a low resolution camera and a high resolution camera that may be used in the target recognition and selection system. For example, possible threats may be queued for interrogation first based on distance to the targets.

The specific examples are not limiting and may be combined in order to provide a system that incorporates features of all or any combination of the examples, as will be recognized by a person in the art. For example, the beam reducer/lenslet array bundle of FIG. 12 may be combined with one or more of the detectors 62, 63, 65 of FIG. 9, and/or the beam expander/beam diverger of FIG. 10 may be combined with one or more of the output channels of the multi-wavelength laser head 12 of FIG. 1, for example. Thus, nothing prevents the combination of features from one or more of the examples in the claims that eventually issue. A single wavelength source beam means that the source beam of the laser system is not provided by multiple laser elements having different wavelengths. Instead, a source beam is supplied by a laser element having its characteristic wavelength, which may be processed by the laser system to provide a plurality of wavelengths in an output beam provided by the laser system, for example. Nothing herein implies or should be taken as suggesting that a single wavelength means that a laser element is characterized by other than what is known in the art for laser elements; however, this application does not foreclose the use of technologies later developed in the laser system described herein, either.

| Telescope Parameters | Example A | Example B |
| --- | --- | --- |
| Primary's Diameter | 340 mm | 150 mm |
| Primary's Radius of curvature | 1450 mm | 300 mm |
| Primary's Conic constant | 0 | −0.8326 |
| Secondary's Diameter | 110 mm | 25 mm |
| Secondary's Radius of curvature | 804.75 | 50 mm |
| Secondary's Conic constant | 0 | 0 |

What is claimed is:

1. A laser detection system for use in stand-off detection of electromagnetic signatures of substances on a surface of a target, the system comprising:
    a laser system comprising optical elements and a source for producing an output beam of the laser system;
    a telescope system arranged with the laser system such that the output beam is directed through the telescope system via an optical component, the optical component comprising a reflective surface for reflecting the output beam, the electromagnetic signatures or both the output beam and the electromagnetic signatures, such that the output beam is directed onto the surface of the target through the telescope system and the electromagnetic signatures of substances on the surface of the target are captured through the same telescope system and are directed by the telescope system to the optical component;
    a detector system comprising an optical system, at least one spectrometer operatively coupled to the optical system, and a processing unit such that electrical signals from the at least one spectrometer are analyzed by the processing unit, the optical system of the detector system being optically coupled to the telescope system via the optical component; and
    a control unit controlling the laser system, the telescope system and the detector system, such that signatures are capable of being detected at a stand-off distance, wherein the optical elements of the laser system include a variable beam expander and a variable beam diverger, operatively arranged such that at least a portion of the output beam of the laser system passes through the variable beam expander and the variable beam diverger prior to being directed to the telescope system.

2. The system of claim 1, further comprising a rangefinder electrically coupled with the control unit, wherein the variable beam expander and the variable beam diverger include movable components capable of focusing the at least a portion of the output beam on the surface of the target under control of the control unit based on signals received by the control unit from the rangefinder, and the control unit controls movement of the movable components of the variable beam expander and the variable beam diverger in combination with movement of a secondary mirror of the telescope system in relation to a primary mirror of the telescope system.

3. The system of claim 1, wherein the variable beam expander and the variable beam diverger are controlled by the control unit such that the output beam exits the telescope system such that the output beam is eye safe.

4. The system of claim 3, wherein the output beam is collimated.

5. The system of claim 1, wherein the optical system of the detector system comprises:
    a beam reducer;
    a lenslet array; and
    an optical fiber bundle having a plurality of optical fibers operatively arranged such that at least a portion of the signatures are directed through the beam reducer, are directed through the lenslet array and are directed into a plurality of the plurality of optical fibers, such that signatures are directed by the plurality of the plurality of optical fibers to the at least one spectrometer.

6. The system of claim 5, wherein the plurality of optical fibers are operatively arranged such that the signatures are directed onto a central portion of the optical fiber bundle and are output from a linear array of the plurality of optical fibers.

7. The system of claim 6, wherein the linear array of the plurality of optical fibers are directed through a linear aperture slit of the at least one spectrometer.

8. The system of claim 7, wherein the lenslet array comprises a 10×10 square lenslet array, defining an outer square of the lenslet array.

9. The system of claim 8, wherein the optical fiber bundle comprises 81 fibers disposed in an array of fibers contained within a circle circumscribed within the outer square of the lenslet array.

10. The system of claim 2, wherein power and wavelength of the output beam is eye safe as emitted by the laser detection system, and the control unit selects a focal length of the output beam of the laser system, a focal length of the telescope system and a time delay for triggering activation of the at least one spectrometer of the detector system such that electromagnetic signatures of substances on the surface of the target are capable of being detected at stand off distances up to fifty meters or greater from the telescope system.

11. The system of claim 2, wherein the control unit selects a focal length of the output beam of the laser system, a focal length of the telescope system and a time delay for triggering activation of the at least one spectrometer of the detector system such that electromagnetic signatures of substances on the surface of the target are capable of being detected at stand off distances up to one hundred meters or greater from the telescope system.

12. The system of claim 1, wherein the control unit selects a focal length of the output beam of the laser system, a focal length of the telescope system and a time delay for triggering activation of the at least one spectrometer of the detector system such that electromagnetic signatures of substances on the surface of the target are capable of being detected at stand off distances up to three hundred meters or greater from the telescope system.

13. The system of claim 1, wherein the source of the laser system produces the output beam with a single wavelength, and the optical elements of the laser system are arranged such that the optical elements produce a modified output beam selectively comprising more than one wavelength from the single wavelength of the output beam produced by the source of the laser system, each of at least two different wavelengths being capable of stimulating Raman signatures from substances on the surface of the target, each of the at least two different wavelengths of the modified output beam being directed to the telescope system via the same optical component coupling the telescope system with the laser system, wherein the optical component comprises coatings capable of reflecting the at least two different wavelengths of the modified output beam.

14. The system of claim 2, further comprising a targeting system comprising a mirror, such that the output beam emitted from the telescope system is directed to the targeting system and any signatures incident on the targeting mirror of the targeting system is directed to a primary mirror of the telescope system, wherein the mirror of the targeting system is capable of redirecting the output beam onto the surface of the target without moving any of the laser system, the detector system or the telescope system.

15. The system of claim 14, wherein the targeting system is capable of redirecting an azimuth and an elevation of the output beam without moving any of the laser system, the detector system or the telescope system.

16. The system of claim 15, wherein the targeting system includes a user interface for selecting targets using the targeting system.

17. The system of claim 15, wherein the targeting system automatically selects targets under control of the control unit.

18. The system of claim 17, wherein the targeting system automatically tracks selected targets under control of the control unit.

19. The system of claim 15, wherein the control unit controls the targeting system, determines a range to a selected target using the rangefinder, moves the movable components of the variable beam expander and the variable beam diverger, moves the secondary mirror of the telescope system in relation to a primary mirror of the telescope system, and operatively activates the at least one spectrometer at a predefined time such that the laser detection system is capable of stand-off distances up to one hundred meters.

20. The system of claim 1, wherein the at least one spectrometer of the detector system is a plurality of spectrometers and the optical system of the detector system comprises at least one dichroic or multi-chroic filter that redirects one range of wavelengths of the signatures received by the detector system to a first one of the plurality of spectrometers and a second range of wavelengths of the signatures received by the detector system to a second one of the plurality of spectrometers.

* * * * *